US009234047B2

(12) United States Patent
Kellermann et al.

(10) Patent No.: US 9,234,047 B2
(45) Date of Patent: Jan. 12, 2016

(54) PREPARING HAPTEN-SPECIFIC ANTIBODIES AND THEIR APPLICATION FOR IMMUNODIAGNOSTICS AND RESEARCH

(75) Inventors: Gottfried H. Kellermann, Hudson, WI (US); Han J. G. Huisman, Osceola, WI (US)

(73) Assignee: Pharmasan Labs, Inc., Osceola, WI (US)

( * ) Notice: Subject to any disclaimer, the term of this patent is extended or adjusted under 35 U.S.C. 154(b) by 24 days.

(21) Appl. No.: 13/508,432

(22) PCT Filed: Nov. 8, 2010

(86) PCT No.: PCT/US2010/055849
§ 371 (c)(1),
(2), (4) Date: Jun. 26, 2012

(87) PCT Pub. No.: WO2011/057200
PCT Pub. Date: May 12, 2011

(65) Prior Publication Data
US 2012/0295287 A1    Nov. 22, 2012

Related U.S. Application Data

(60) Provisional application No. 61/259,020, filed on Nov. 6, 2009.

(51) Int. Cl.
*G01N 33/566* (2006.01)
*C07K 1/113* (2006.01)
*C07K 16/18* (2006.01)
*C07K 16/44* (2006.01)
*G01N 33/94* (2006.01)

(52) U.S. Cl.
CPC ............ *C07K 16/44* (2013.01); *G01N 33/9406* (2013.01); *C07K 2317/33* (2013.01)

(58) Field of Classification Search
CPC ..... G01N 33/9406; G01N 33/53; C07K 16/44
See application file for complete search history.

(56) References Cited

U.S. PATENT DOCUMENTS

| 4,122,078 | A | 10/1978 | Yoshioka et al. |
| 4,908,322 | A | 3/1990 | Jacobson et al. |
| 5,033,252 | A | 7/1991 | Carter |
| 5,052,558 | A | 10/1991 | Carter |
| 5,323,907 | A | 6/1994 | Kalvelage |
| 2007/0087453 | A1 | 4/2007 | Suri et al. |

FOREIGN PATENT DOCUMENTS

EP    558566    10/1991

OTHER PUBLICATIONS

Mart'ianov et al. Preparation of antibodies and development of enzyme-linked immunosorbent assay for nonylphenol. Intern. J. Environ. Anal. Chem. 2004, vol. 84, No. 13, pp. 965-978.*
Vhagnaud et al. Monoclonal antibodies against glutaraldehyde-conjugated dopamine. J. Neurochemistry 1987, vol. 49, No. 2, pp. 487-494.*
Gammelsaeter et al. Glycine, GABA and their transporters in pancreatic islets of Langerhans: evidence for a paracrine transmitter interplay. Journal of Cell Science 2004, vol. 117, No. 17, pp. 3749-3758.*
Geffard et al. Antibodies to dopamine: radioimmunological study of specificity in relation to immunocytochemistry. Journal of Neurochemistry 1984, vol. 42, No. 6, pp. 1593-1599.*
Meyer et al. Antibodies against neuroactive amino acids and neuropeptides. I. New two-step procedure for their conjugation to carrier proteins and the production of an anti-met-enkephalin antibody reactive with glutaraldehyde-fixed tissues. Journal of Histochemistry and Cytochemistry 1991, vol. 39, No. 6, pp. 749-760.*
Chakrabarti et al. A monoclonal antibody to a cytoskeletal protein selectively recognizing malignanat neuroectodermal tumors. Hybridoma 1994, vol. 13, No. 6, pp. 491-497.*
Greg T. Hermanson, Bioconjugate Chemistry 1996, Academic Press, San Diego, CA.*
International Search Report and Written Opinion in International Application No. PCT/US2010/055849, dated Mar. 4, 2011, 12 pages.
International Preliminary Report on Patentability in International Application No. PCT/US2010/055849, dated May 8, 2012, 10 pages.
"Immunology," *Short Protocols in Molecular Biology*, Chapter 11, Edited by Ausubel, F.M et al., 1992, 56 pages.
Cole et al., "The EBV-Hybridoma Technique and Its Application to Human Lung Cancer," *Monoclonal Antibodies and Cancer Therapy*, 1983, pp. 77-96.
Cote et al., "Generation of human monoclonal antibodies reactive with cellular antigens," *Proc. Natl. Acad. Sci. USA*, 1983, 80:2026-2030.
Flohe et al., "Kinetics of Purified Catechol O-Methyltransferase," *Biochim. Biophys. Acta.*, 1970, 200:469-476.
Harthe et al., "Direct radioimmunoassay of 6-sulfatoxymelatonin in plasma with use of an iodinated tracer," *Clin. Chem.*, 1991, 37(4):536-539.

(Continued)

*Primary Examiner* — Shafiqul Haq
(74) *Attorney, Agent, or Firm* — Fish & Richardson P.C.

(57) ABSTRACT

This document provides methods and materials related to detecting neurotransmitters and other biologically active small molecules. For example, methods for detecting and measuring hapten levels in a biological sample using antibodies specific for conjugated haptens are provided.

41 Claims, 4 Drawing Sheets

(56) References Cited

OTHER PUBLICATIONS

Iinuma et al., "Radioimmunoassay of metanephrine and normetanephrine to diagnosis of pheochromocytoma," *Clin. Chem.*, 1986, 32(10):1879-1883.

Knoll et al., "Problems in the development of radioimmunoassay of catecholamines," *J. Clin. Chem. Clin. Biochem.*, 1984, 22:741-749.

Kohler et al., "Continuous cultures of fused cells secreting antibody of predefined specificity," *Nature*, 1975, 256:495-497.

Kozbor et al., "The Production of monoclonal antibodies from human lymphocytes," *Immunology Today*, 1983, 4:72-79.

Tilgmann et al., "Purification and partial characterization of rat liver soluble catechol-O-methyltransferase," *FEBS*, 1990, 264:95-99.

*Thermo Scientific Avidin-Biotin Technical Handbook*, Thermo Fisher Scientific Inc., 2009, 51 pages.

*Qdot Antibody Conjugation Kits*, Invitrogen Detection Technologies, Mar. 2008, 9 pages.

\* cited by examiner

PREPARING HAPTEN-SPECIFIC ANTIBODIES AND THEIR APPLICATION FOR IMMUNODIAGNOSTICS AND RESEARCH

CROSS-REFERENCE TO RELATED APPLICATION

This application is a National Stage application under 35 U.S.C. 371 of International Application No. PCT/US2010/055849, having an International Filing Date of Nov. 8, 2010, which claims priority under 35 U.S.C. §119(e) to U.S. Provisional Application Ser. No. 61/259,020, filed on Nov. 6, 2009, entitled PREPARING HAPTEN-SPECIFIC ANTIBODIES, the disclosures of which are incorporated herein by reference.

BACKGROUND

1. Technical Field

This document provides methods and materials related to detecting and quantifying biologically active small molecules. For example, this document provides methods for detecting and measuring biologically active small molecule levels in a biological sample.

2. Background Information

Neurotransmitters, biogenic amines, biogenic de-aminated neurotransmitters and their derivatives, metabolites, and precursors are biologically active small molecules which have a systemic influence on the body's nervous system and are the predominate actuators of the central nervous system. Numerous diseases, including cognitive, mood, and motor function disorders, are associated with imbalances in neurotransmitter levels. For example, impairment of the dopamine system is implicated in schizophrenia, a mental disease marked by disturbances in thinking and emotional reactions, while clinical depression is associated with an imbalance in serotonin levels. Parkinson's disease is correlated reduced levels of dopamine. Increased levels of excitatory amino acids such as glutamate and aspartate are correlated with attention deficit hyperactivity disorder (ADHD) and sleeping disorders.

Typically, biologically active small molecules do not induce the formation of antibodies by themselves, but can in some circumstances induce antibodies when bound to a higher molecular weight molecule.

SUMMARY

This document provides methods and materials related to detecting biologically active small molecules. As described herein, immunogens can be generated from neurotransmitters and other biologically active small molecules (referred to as "neuroactive haptens" or "haptens" herein) coupled to a higher molecular weight molecule such as a polypeptide or polypeptide fragment. For example, a hapten can be conjugated to a polypeptide to form an immunogenic composition for use in generating hapten-polypeptide conjugate specific antibodies (also referred to as hapten-specific antibodies or hapten-conjugate specific antibodies herein). Hapten-polypeptide conjugates can be referred to as "polypeptide conjugated haptens" or "conjugated haptens" also herein. In some cases, antibodies specific for the conjugated haptens provided herein can be used to detect and measure neurotransmitter or other small molecule levels in a biological sample using an immunoassay. As described herein, this document provides, for example, methods and materials by which clinicians and other professionals can detect the presence of and measure neurotransmitter levels in a patient's biological sample using the described antibodies and described sample preparations. Such detection methods can have substantial value for clinical and research use.

As used herein, the terms "one-step" or "two-step," when used to describe a method herein, are non-limiting in that the described method can include at least the one or two described steps, but can include additional steps before, between, or after the described step(s).

In one aspect, this document features methods for conjugating a hapten to a polypeptide. The one-step method comprises contacting a hapten to a polypeptide in the presence of a conjugation reagent to form a mixture. The molar ratio of the hapten to the polypeptide in the mixture is low. The ratio of the polypeptide to the hapten can be between about 10:1 (w/w) and about 10:0.1 (w/w). The polypeptide can be a carrier protein or fragment thereof. The carrier protein can be selected from the group consisting of bovine serum albumin (BSA), thyroglobuline (TG), keyhole limpet hemocyanin (KLH), gelatin, and ovalbumin (OVA), or a fragment thereof. The hapten can be a neurotransmitter or biogenic amine. The neurotransmitter can comprise an amine. The hapten can comprise an amine. The neurotransmitter can be selected from the group consisting of γ-amino-butyric acid (GABA), L-glutamic acid, L-theanine, agmatine, epinephrine, norepinephrine, tyramine and tryptamine. The hapten can be a non-amine containing hapten. The non-amine containing hapten can be selected from the group consisting of dihydroxyphenyl acetic acid (DOPAC), 5-HIAA, DHPG, and 6-sulfatoxy-melatonin.

In another aspect, this document features a method for conjugating a non-amine containing hapten to a polypeptide. The conjugating can comprise contacting the polypeptide to the non-amine containing hapten in the presence of a conjugation reagent under conditions appropriate for a Mannich condensation reaction to occur.

In a further aspect, this document features a one-step method for conjugating a polypeptide and a hapten. The conjugating can comprise contacting the polypeptide to the hapten in the presence of a suboptimal final concentration of a conjugation reagent. The conjugation reagent can comprise an aldehyde moiety. The suboptimal final concentration of a conjugation reagent can be between about 5 mM and about 10 mM.

In another aspect this document features a one-step method for preparing a biological sample for detecting a hapten of interest. The method comprises contacting a conjugation reagent to a biological sample whereby the hapten of interest, if present in the biological sample, will conjugate with the conjugation reagent and the endogenous protein or peptide fragments in the biological sample to form a polypeptide-hapten conjugate. The biological sample can be a clinical sample. The biological sample can be selected from the group consisting of blood, plasma, serum, platelets, urine, cerebrospinal fluid, sputum, tears, amniotic fluid, vitreous humor, and saliva. The method can further comprise quenching unreacted conjugation reagent from the contacted biological sample.

In another aspect, this document features a two-step method for preparing a biological sample for detecting a hapten of interest. The method comprises contacting a conjugation reagent to a polypeptide to form a composition, and contacting the composition to the biological sample, whereby the hapten of interest, if present in the biological sample, will conjugate with the composition to form polypeptide-hapten conjugates. The biological sample can be a clinical sample. The biological sample can be selected from the group consisting of blood, plasma, serum, platelets, urine, cerebrospinal fluid, sputum, tears, amniotic fluid, vitreous humor, and saliva. The method can further comprise quenching unreacted conjugation reagent from the contacted biological sample.

In another aspect, this document features a method for generating an immunogenic composition. The one-step method comprises conjugating a hapten to a polypeptide. The conjugating can comprise contacting a polypeptide to a hapten in the presence of a conjugation reagent to form a mixture. The molar ratio of the hapten to the polypeptide in said mixture can be low. The ratio of the polypeptide to the hapten can be between about 10:1 (w/w) and about 10:0.1 (w/w).

In a further aspect, this document features a method for generating an immunogenic composition. The one-step method comprises conjugating a polypeptide to a hapten, wherein the conjugating comprises contacting the polypeptide to the hapten in the presence of a suboptimal final concentration (e.g., about 5-10 mM) of a conjugation reagent.

In another aspect, this document features a method for generating an immunogenic composition. The two-step method comprises treating a polypeptide with a conjugation reagent to form a treated polypeptide, and contacting the treated polypeptide to a hapten of interest to form a polypeptide-hapten conjugate.

In another aspect, this document features a method for generating an immunogenic composition. The two-step method comprises treating a polypeptide with a conjugation reagent to form a treated polypeptide, and contacting the treated polypeptide to a hapten of interest to form a polypeptide-hapten conjugate, wherein the contacting step is performed at a low final ratio of hapten to polypeptide.

In a further aspect, this document features a method for generating an immunogenic composition. The method comprises treating a polypeptide with a conjugation reagent to form a treated polypeptide, and contacting the treated polypeptide to a hapten of interest to form a polypeptide-hapten conjugate, wherein the treating step is performed at a final concentration of about, e.g., 500 mM, of the conjugation reagent.

In another aspect, this document features a method for generating an immunogenic composition. The one-step method comprises conjugating a polypeptide to a hapten, wherein the conjugating comprises contacting the polypeptide to the hapten in the presence of a suboptimal final concentration of a conjugation reagent and wherein a molar ratio of the hapten to the polypeptide is low.

In another aspect, this document features a method for obtaining polyclonal antibodies specific for a conjugated hapten of interest. The method comprises immunizing an animal with the immunogenic composition obtained by the methods of provided herein; isolating serum from said immunized animal; and collecting the polyclonal antibodies specific for the conjugated hapten from the serum.

In a further aspect, this document features an isolated polyclonal antibody specific for agmatine, wherein the antibody is not specific for conjugated glutamic acid, conjugated lysine, conjugated arginine, or conjugated cadaverine. The isolated antibody can demonstrate greater than about $1:1\times10^4$ cross-reactivity with conjugated glutamic acid, conjugated lysine, conjugated arginine, or conjugated cadaverine. The isolated antibody can comprise a detectable label. The detectable label can comprise a fluorescent, luminescent, chemiluminescent, bioluminescent, radioactive, or enzymatic label.

In another aspect, this document features isolated polyclonal antibodies specific for one or both of the different stereoisomers of epinephrine (e.g., polyclonal antibodies specific for both (+/−) and polyclonal antibodies specific for (−)) wherein each population of polyclonal antibodies is not specific for conjugated metanephrine, conjugated norepinephrine, or conjugated dopamine. The isolated polyclonal antibody can demonstrate greater than about $1:1\times10^4$ cross-reactivity with conjugated metanephrine, conjugated norepinephrine, or conjugated dopamine. The isolated antibody can comprise a detectable label. The detectable label can comprise a fluorescent, luminescent, chemiluminescent, bioluminescent, radioactive, or enzymatic label.

In another aspect, this document features an isolated polyclonal antibody specific for L-theanine, wherein the antibody is not specific for conjugated glutamate, conjugated glutamine, conjugated GABA, or conjugated β-PEA. The isolated antibody can demonstrate greater than about $1:1\times10^4$ cross-reactivity with conjugated glutamate, conjugated glutamine, conjugated GABA, or conjugated β-PEA. The isolated antibody can comprise a detectable label. The detectable label can comprise a fluorescent, luminescent, chemiluminescent, bioluminescent, radioactive, or enzymatic label.

In another aspect, this document features an isolated polyclonal antibody specific for tyramine, wherein the antibody is not specific for conjugated tyrosine, 1-dopa and dopamine. The isolated antibody can demonstrate greater than about $1:1\times10^4$ cross-reactivity with conjugated tyrosine, conjugated 1-dopa, or conjugated dopamine. The isolated antibody can comprise a detectable label. The detectable label can comprise a fluorescent, luminescent, chemiluminescent, bioluminescent, radioactive, or enzymatic label.

In another aspect, this document features an isolated polyclonal antibody specific for tryptamine, wherein the antibody is not specific for conjugated tryptophan, 5-HTP and conjugated serotonin. The isolated antibody can demonstrate greater than about $1:1\times10^4$ cross-reactivity with conjugated tryptophan, conjugated 5-HTP, or conjugated serotonin. The isolated antibody can comprise a detectable label. The detectable label can comprise a fluorescent, luminescent, chemiluminescent, bioluminescent, radioactive, or enzymatic label.

In another aspect, this document features an isolated polyclonal antibody specific for 6-sulfatoxy-melatonin wherein the antibody is not specific for conjugated melatonin and N—Ac—HT. The isolated antibody can demonstrate greater than about $1:1\times10^4$ cross-reactivity with conjugated melatonin, conjugated N—Ac—NT. The isolated antibody can comprise a detectable label. The detectable label can comprise a fluorescent, luminescent, chemiluminescent, bioluminescent, radioactive, or enzymatic label.

In another aspect, this document features a method for purifying a population of polyclonal antibodies having affinity for a conjugated hapten of interest. The method comprises depleting from the population antibodies having affinity for unconjugated polypeptide, wherein the depleting comprises using an unconjugated polypeptide affinity column.

In another aspect, this document features a method for purifying a population of polyclonal antibodies having affinity for a conjugated hapten of interest. The method comprises depleting from said population antibodies having affinity for polypeptide-conjugation reagent species, wherein the depleting comprises using a polypeptide-conjugated reagent affinity column.

In a further aspect, this document features a method for increasing the specificity of an polyclonal population of antibodies for a conjugated hapten of interest. The method comprises depleting from the population antibodies having affinity for unconjugated polypeptide, wherein the depleting comprises using an unconjugated polypeptide affinity column.

In another aspect, this document features a method for increasing the specificity of an polyclonal population for a conjugated hapten of interest. The method comprises depleting from the population antibodies having affinity for polypeptide-conjugation reagent species, wherein the depleting comprises using a polypeptide-conjugated reagent affinity column.

In another aspect, this document features methods for detecting hapten of interest in a biological sample. The one-step method comprises treating a biological sample with a conjugation reagent whereby the hapten of interest, if present in the biological sample, will conjugate with the conjugation reagent and the endogenous protein or peptide fragments in the biological sample to form a polypeptide-hapten conjugate. The biological sample can be a clinical sample. The biological sample can be selected from the group consisting of blood, plasma, serum, platelets, urine, cerebrospinal fluid, sputum, tears, amniotic fluid, vitreous humor, and saliva. The method can further comprise quenching unreacted conjugation reagent from the contacted biological sample. The two-step method comprises treating a polypeptide with a conjugation reagent to form a treated polypeptide; contacting the treated polypeptide to the biological sample, wherein the contacting forms a polypeptide-hapten conjugate if the hapten is present in the biological sample; contacting an antibody specific for hapten to the contacted biological sample; and determining if the antibody binds to the polypeptide-hapten conjugate if present in the biological sample using an immunoassay. The method can further comprise measuring the level of the hapten if present in the biological sample. The measuring can comprise an immunoassay. The antibody can comprise a detectable label. The detectable label can comprise a fluorescent, luminescent, chemiluminescent, bioluminescent, radioactive, or enzymatic label.

In a further aspect, this document features a method for detecting agmatine in a biological sample. The one-step method comprises treating a biological sample with a conjugation reagent whereby agmatine, if present in the biological sample, will conjugate with the conjugation reagent and the endogenous protein or peptide fragments in the biological sample to form a polypeptide-hapten contacting an antibody specific for agmatine to the contacted biological sample; and determining if the antibody binds to the polypeptide-agmatine conjugate if present in the biological sample using an immunoassay.

In another aspect, this document features a method for measuring agmatine levels in a biological sample. The one-step method comprises treating a biological sample with a conjugation reagent whereby agmatine, if present in the biological sample, will conjugate with the conjugation reagent and the endogenous protein or peptide fragments in the biological sample to form a polypeptide-hapten; contacting an antibody specific for agmatine to the contacted biological sample; determining if the antibody binds to a conjugate of the carrier protein and agmatine if present in the biological sample using an immunoassay; and measuring an agmatine level in said biological sample, if agmatine is present in said biological sample.

In a further aspect, this document features a method for detecting L-theanine in a biological sample. The one-step method comprises treating a biological sample with a conjugation reagent whereby L-theanine, if present in the biological sample, will conjugate with the conjugation reagent and the endogenous protein or peptide fragments in the biological sample to form a polypeptide-hapten contacting an antibody specific for L-theanine to the contacted biological sample; and determining if the antibody binds to the polypeptide-L-theanine conjugate if present in the biological sample using an immunoassay.

In another aspect, this document features a method for measuring L-theanine levels in a biological sample. The one-step method comprises treating a biological sample with a conjugation reagent whereby L-theanine, if present in the biological sample, will conjugate with the conjugation reagent and the endogenous protein or peptide fragments in the biological sample to form a polypeptide-hapten; contacting an antibody specific for L-theanine to the contacted biological sample; determining if the antibody binds to a conjugate of the carrier protein and L-theanine if present in the biological sample using an immunoassay; and measuring an L-theanine level in said biological sample, if L-theanine is present in said biological sample.

In a further aspect, this document features a method for detecting tyramine in a biological sample. The one-step method comprises treating a biological sample with a conjugation reagent whereby tyramine, if present in the biological sample, will conjugate with the conjugation reagent and the endogenous protein or peptide fragments in the biological sample to form a polypeptide-hapten contacting an antibody specific for tyramine to the contacted biological sample; and determining if the antibody binds to the polypeptide-tyramine conjugate if present in the biological sample using an immunoassay.

In another aspect, this document features a method for measuring tyramine levels in a biological sample. The one-step method comprises treating a biological sample with a conjugation reagent whereby tyramine, if present in the biological sample, will conjugate with the conjugation reagent and the endogenous protein or peptide fragments in the biological sample to form a polypeptide-hapten; contacting an antibody specific for tyramine to the contacted biological sample; determining if the antibody binds to a conjugate of the carrier protein and tyramine if present in the biological sample using an immunoassay; and measuring an tyramine level in said biological sample, if tyramine is present in said biological sample.

In a further aspect, this document features a method for detecting tryptamine in a biological sample. The one-step method comprises treating a biological sample with a conjugation reagent whereby tryptamine, if present in the biological sample, will conjugate with the conjugation reagent and the endogenous protein or peptide fragments in the biological sample to form a polypeptide-hapten contacting an antibody specific for tryptamine to the contacted biological sample; and determining if the antibody binds to the polypeptide-tryptamine conjugate if present in the biological sample using an immunoassay.

In another aspect, this document features a method for measuring tryptamine levels in a biological sample. The one-step method comprises treating a biological sample with a conjugation reagent whereby tryptamine, if present in the biological sample, will conjugate with the conjugation reagent and the endogenous protein or peptide fragments in the biological sample to form a polypeptide-hapten; contacting an antibody specific for tryptamine to the contacted biological sample; determining if the antibody binds to a conjugate of the carrier protein and tryptamine if present in the biological sample using an immunoassay; and measuring an tryptamine level in said biological sample, if tryptamine is present in said biological sample.

In a further aspect, this document features a method for detecting 6-sulfatoxy-melatonin in a biological sample. The one-step method comprises treating a biological sample with a conjugation reagent whereby 6-sulfatoxy-melatonin, if present in the biological sample, will conjugate with the conjugation reagent and the endogenous protein or peptide fragments in the biological sample to form a polypeptide-hapten contacting an antibody specific for 6-sulfatoxy-melatonin to the contacted biological sample; and determining if the antibody binds to the polypeptide-6-sulfatoxy-melatonin conjugate if present in the biological sample using an immunoassay.

In another aspect, this document features a method for measuring 6-sulfatoxy-melatonin levels in a biological sample. The one-step method comprises treating a biological sample with a conjugation reagent whereby 6-sulfatoxy-melatonin, if present in the biological sample, will conjugate with the conjugation reagent and the endogenous protein or peptide fragments in the biological sample to form a polypeptide-hapten; contacting an antibody specific for 6-sulfatoxy-melatonin to the contacted biological sample; determining if the antibody binds to a conjugate of the carrier protein and 6-sulfatoxy-melatonin if present in the biological sample using an immunoassay; and measuring an 6-sulfatoxy-melatonin level in said biological sample, if 6-sulfatoxy-melatonin is present in said biological sample.

In a further aspect, this document features a method for detecting (and e.g., determining amounts or levels of) one or both of the two stereoisomers of epinephrine ((+) stereoisomer, (−) stereoisomer) in a biological sample. The two-step method comprises treating a polypeptide with a conjugation reagent to form a treated polypeptide; contacting the treated polypeptide to the biological sample, wherein the contacting forms a polypeptide-epinephrine conjugate if epinephrine is present in the biological sample; contacting an antibody (e.g., a polyclonal antibody) specific for one or both of the two stereoisomers of epinephrine to the contacted biological sample (e.g., a polyclonal antibody specific for both (+/−) or a polyclonal antibody specific for (−)); and determining if the antibody binds to the polypeptide-epinephrine conjugate if present in the biological sample using an immunoassay. In some embodiments, the contacted biological sample is contacted with an antibody specific for both the (+/−) stereoisomers, and with an antibody specific for the (−) stereoisomer, either at the same time or at different times and in any order.

In another aspect, this document features a method for measuring the amount of one or both of the two stereoisomers of epinephrine levels in a biological sample. The method comprises treating a carrier protein with a conjugation reagent to form a treated carrier protein; contacting the treated carrier protein to the biological sample, wherein the contacting forms a conjugate of the carrier protein and epinephrine if the epinephrine is present in the biological sample; contacting an antibody (e.g., a polyclonal antibody) specific for one or both of the two stereoisomers of epinephrine to the contacted biological sample (e.g., a polyclonal antibody specific for both (+/−) or a polyclonal antibody specific for (−)); determining if the antibody binds to a conjugate of the carrier protein and epinephrine if present in the biological sample using an immunoassay; and based on said determining, measuring an epinephrine level (e.g., the (−) stereoisomer level, the total (+/−) level, the (+) level, based on the particular polyclonal antibodies used) in the biological sample. In some embodiments, the level of (−) epinephrine is determined. In some embodiments, the total level of epinephrine (e.g., level of both stereoisomers) is determined. In some embodiments, the level of (+) is determined, e.g., by subtracting the (−) level from the (+/−) level.

In a further aspect, this document features isolated polyclonal antibodies specific for one or both epinephrine stereoisomers (e.g., a polyclonal antibody specific for (+/−) and a polyclonal antibody specific for (−)) made according to the methods provided herein. The isolated polyclonal antibody demonstrates greater than about $1:1\times10^4$ cross-reactivity with conjugated metanephrine, conjugated norepinephrine, or conjugated dopamine.

In another aspect, this document features an isolated polyclonal antibody specific for agmatine made according to the methods provided herein. The isolated antibody demonstrates greater than about $1:1\times10^4$ cross-reactivity with conjugated glutamic acid, conjugated lysine, conjugated arginine, or conjugated cadaverine.

In another aspect, this document features an isolated polyclonal antibody specific for L-theanine made according to the methods provided herein. The isolated antibody demonstrates greater than about $1:1\times10^4$ cross-reactivity with conjugated glutamate, conjugated glutamine, conjugated GABA, or conjugated β-PEA.

In another aspect, this document features an isolated polyclonal antibody specific for tryptamine made according to the methods provided herein. The isolated antibody demonstrates greater than about $1:1\times10^4$ cross-reactivity with conjugated tryptophan, conjugated 5-HTP, conjugated 5-HIAA, conjugated 5-HTOL, conjugated N—Ac-5-HT, or conjugated conjugated melatonin.

In another aspect, this document features an isolated polyclonal antibody specific for tyramine made according to the methods provided herein. The isolated antibody demonstrates greater than about $1:1\times10^4$ cross-reactivity with conjugated norepinephrine, conjugated dopamine, conjugated epinephrine, conjugated phenylalanine, conjugated tyrosine, conjugated L-DOPA, conjugated β-PEA, conjugated 3-methoxytyramine, conjugated normetanephrine, conjugated metanephrine, conjugated DOPAC, or conjugated DHPG.

In another aspect, this document features an isolated polyclonal antibody specific for 6-sulfatoxy-melatonin made according to the methods provided herein. The isolated antibody demonstrates greater than about $1:1\times10^4$ cross-reactivity with conjugated melatonin and N-AC—HT.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
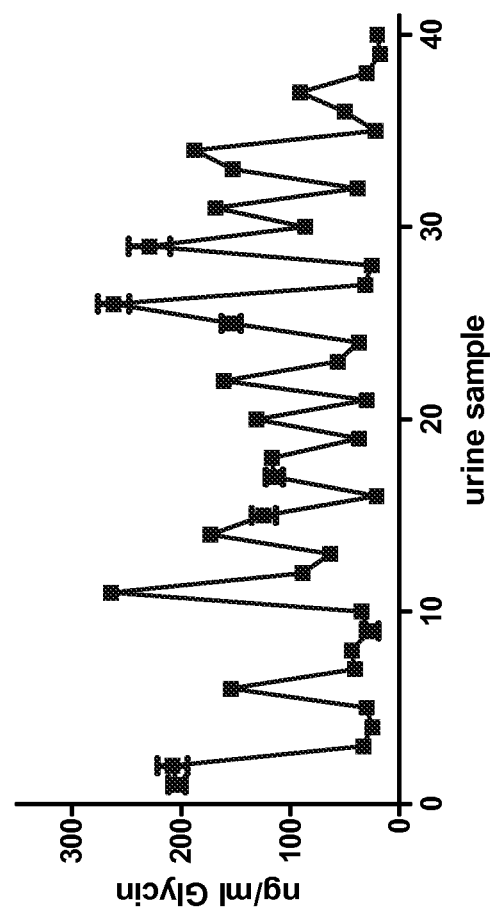
FIG. 1 depicts a glycine assay of urine samples. Glycine determination was performed in duplicate for 40 random urine samples. Wells were coated in TG-glycine (1:800). The primary antibody, IgG-glycine (1:800), was obtained with an immunogenic composition comprising a KLH-glycine conjugate. The secondary antibody was a goat antibody raised against rabbit IgG and conjugated to alkaline phosphatase (GR-AP) (1:15,000).

This document provides methods and materials related to detecting biologically active small molecules. The term "biologically or neurologically active small molecules" is used interchangeably with the term "hapten" herein. Once bound to a higher molecular weight molecule, hapten conjugates can be used as immunogenic compositions, e.g., to induce the formation of antibodies to the hapten-conjugates. Hapten-specific antibodies and methods for using the antibodies described herein can be used to detect the presence of a hapten of interest (e.g., a hapten of interest conjugated to a polypeptide) in a biological sample.

The terms "antibody" and "antibodies" include polyclonal antibodies, monoclonal antibodies, humanized or chimeric antibodies, single chain Fv antibody fragments, Fab fragments, F(ab)$_2$ fragments, and diabodies. Polyclonal antibodies are heterogeneous populations of antibody molecules that are specific for a particular antigen, while monoclonal antibodies are a homogeneous population of one isotype of an antibody (i.e., IgG, IgM) to a particular epitope contained within an antigen. A chimeric antibody is a molecule in which different portions are derived from different animal species, such as those having a variable region derived from a mouse monoclonal antibody and a human immunoglobulin constant region. The term "epitope" refers to an antigenic determinant on an antigen to which an antibody binds. Epitopes of larger molecules usually consist of chemically active surface groupings of molecules such as amino acids, sugar side chains, or chemical moieties (e.g., from organic compounds) and typically have specific three-dimensional structural characteristics as well as specific charge characteristics. Epitopes can consist of a series of contiguous amino acids, e.g., 5 contiguous amino acids. In some cases, an epitope can be a discontinuous epitope, e.g., the epitope is a particular arrangement of amino acids in space that results from the secondary, tertiary, and/or quaternary folding of a polypeptide. In some other cases, an epitope can consist of a modified amino acid side chain, e.g., a phosphorylated tyrosine, serine, or threonine. Epitopes of haptens usually comprise chemically active surface groups, e.g.: OH; COOH; H; $NH_2$. The bindings sites for antibodies are small, and interaction takes place mainly via charge interactions, or hydrophobicity or hydrophilicity. Polyclonal antibodies can be particularly useful for the materials and methods provided herein.

Immunogenic Compositions

This document provides methods and materials for preparing immunogenic compositions. Immunogenic compositions can be obtained by conjugating a hapten of interest to a higher molecular weight molecule. Examples of haptens appropriate for the methods provided herein can include small molecule neurotransmitters and biogenic amines (e.g., amino acids or derivatives thereof) or neurotransmitter metabolites of the central, sympathetic, and parasympathetic nervous systems. For example, neuroactive-haptens can include, without limitation, serotonin, norepinephrine, dopamine, histamine, and acetylcholine. In some cases, haptens can include γ-aminobutyric acid (GABA); L-glutamic acid; epinephrine; 3,4-hydroxy-phenylacetic acid (DOPAC), and 5-hydroxyindoleacetic acid (5-HIAA). In some cases, haptens can include agmatine, norvaline, L-ornithine, DL-5-hydroxylysine, 2-aminobutyric acid, L-glutamate-γ-methyl ester, L-glutamate-γ-ethyl ester, L-glutamate-γ-hydrazide, poly-L-glutamate, poly-L-glycine, 4-amino-3-(4-chlorophenyl)-butanoic acid (baclofen), O-phospho-L-serine, β-alanine, L-tryptophan, L-tryptamine, 5-hydroxy-D,L-tryptophan (5-HTP), 5-hydroxytryptamine (5-HT), 5-hydroxytryptophol (5-HTOL), N—Acetyl-5-hydroxytryptamine (N—Ac-5-HT), melatonin, 6-hydroxymelatonin, D, L-norepinephrine, DL-dopamine, D,L-epinephrine, L-phenylalanine, L-tyrosine, L-dihydroxyphenylalanine (L-DOPA), β-phenylethylamine (β-PEA), D,L-tyramine, D,L-octopamine, 3-hydroxy-4-methoxytyramine, 3-methoxytyramine, DL-normetanephrine, D,L-metanephrine, S-(−)-carbidopa, 6-hydroxydopamine, and dihydroxyphenylglycol (DHPG). Other haptens appropriate for the methods described herein can include, without limitation, steroids (e.g., estrogen, progesterone, testosterone, estradiol), vitamins (e.g., vitamin B12, folic acid), neuropeptides (e.g., vasopressin, oxytocin, neuropeptide Y), and antibiotics. As used above, the terms "DL" or "D,L" are not meant to imply a racemic mixture, but are meant to indicate that the hapten can be the "D" or the "L" isomer, or both.

Higher molecular weight molecules appropriate for preparing immunogenic compositions can be polypeptides. For the methods described herein, a "polypeptide" can be a whole (i.e., intact) polypeptide or a polypeptide fragment. Polypeptide fragments can be any appropriate size such as about 3,000 Daltons or greater (e.g., 3,000; 4,000; 5,000; 6,000 Daltons, or more). In some cases, a higher molecular weight molecule can be a carrier protein or a fragment thereof. Examples of carrier proteins include bovine serum albumin (BSA), cationized BSA, thyroglobuline from porcine (TG), keyhole limpet hemocyanin (KLH), ovalbumin (OVA), tetanus toxoid, or gelatin.

Any appropriate method of conjugating haptens to higher molecular weight molecules can be used. In some cases, a one-step reaction can be used. The one-step reaction can involve contacting a conjugation reagent, a higher molecular weight molecule such as a polypeptide or polypeptide fragment, and a hapten of interest. The one step reaction can result in conjugations between polypeptides, between conjugation reagents, and between the hapten and the polypeptide. The formation of hapten-polypeptide conjugates can be confirmed by any appropriate method including, without limitation, spectrophotometry, isoelectric focusing, NMR and Mass Spectrometry, and SDS-PAGE.

In some cases, a two-step reaction can be used to conjugate a hapten of interest to a higher molecular weight molecule. In the first step, a polypeptide can be contacted with a conjugation reagent to form a "pre-treated polypeptide." A pre-treated polypeptide can have the following characteristics: a bi-valent conjugation reagent can be bound to the polypeptide at one of two conjugation moieties of the conjugation reagent (e.g., a di-aldehyde), and the majority of the second conjugation moiety can remain free to conjugate to a hapten in the second step to form a polypeptide-hapten conjugate. In the second step, the pre-treated polypeptide can be contacted to the hapten of interest, optionally in the presence of a conjugation reagent, which can be the same or different than the conjugation reagent employed in the first step. Haptens can react with the pre-treated polypeptide to form polypeptide-hapten conjugates.

To effect cross-linking (e.g., conjugating) of a hapten to a higher molecular weight molecule by either the one-step or two-step conjugation method, one or more conjugation reagents can be used. A conjugation reagent can include one or more conjugation moieties, e.g., chemical moieties suitable for conjugating (e.g., cross-linking) to a moiety on a higher molecular weight molecule or a hapten of interest. In some cases, a conjugation reagents can be a monovalent aldehyde (e.g., formaldehyde), bivalent aldehyde (e.g., glutaric aldehyde), hydrozine, carbodiimide, or diisocyanate. For amine-containing haptens, a bivalent aldehyde such as glutaric aldehyde ($OHCCH_2CH_2CH_2CHO$) can be used as a conjugation reagent. In such a case, adding conjugation reagent glutaric acid to a primary amine-containing hapten can form Schiff bases (imides) with the amino group of the polypeptide. In some cases, the hapten contains a secondary amine and the addition of an aldehyde can promote the formation of a hemiacetal and an imide with the amino group of the polypeptide. For example, epinephrine ($C_6H_3(OH)_2$—$CH(OH)$—$CH_2$—$NH$—$CH_3$) contains a secondary amine which forms a hemiacetal and an imide with the polypeptide upon the addition of glutaric acid.

For non-amine containing haptens, a monovalent aldehyde such as formaldehyde can be used as a conjugation reagent to prepare hapten-carrier protein conjugates. For example, the Mannich condensation reaction can be used. Generally, a Mannich condensation reaction involves a bivalent or monovalent aldehyde (e.g., formaldehyde) and a compound with an active hydrogen. Aldehydes, ketones, phenols, and tyrosine- and tryptophan-backbones are examples of compounds having an active hydrogen atom. To make hapten-polypeptide conjugates, a hapten lacking nucleophilic groups can be conjugated to the amine functional group on the polypeptide in the presence of an aldehyde (e.g., formaldehyde).

Using either the one-step or two-step conjugation method, the inventors have found that specific antibodies can be obtained by conjugating a hapten to a polypeptide using low ratios of hapten to polypeptide. For example, a low ratio of hapten to polypeptide ratio can be determined based on the carrier polypeptide's molar concentration of an amino acid such as lysine. If a hapten is conjugated to a carrier polypeptide has one lysine residue, a molar concentration of 0.5 mM of the carrier polypeptide corresponds to 0.5 mM of lysine for the conjugation reaction. Similarly, if a carrier polypeptide has two lysine residues, a molar concentration of 0.5 mM of the polypeptide corresponds to 1.0 mM molar concentration of available lysine to cross-react. In some cases, lysine can be the amino acid used in the conjugating reaction, and the ratio of hapten to polypeptide can be about 1 mM hapten to about 1 mM lysine (in carrier polypeptide). In another case, a ratio of hapten to polypeptide can be about 0.1 mM hapten to about 1 mM lysine.

Similarly, the inventors have also found that using suboptimal concentrations of the conjugation reagent results in the preparation of immunogenic compositions with minimal nonspecific conjugation. For example, 5-10 mM of the conjugation reagent glutaric aldehyde results in the preparation of immunogenic compositions with minimal nonspecific conjugation. High conjugation reagent concentrations may promote nonspecific conjugation and uncontrolled polymerization of the polypeptide. In some cases, conjugation reagent can be used at a final concentration of between about 5 mM to about 10 mM (e.g., about 5 mM, 5.5 mM, 6 mM, 6.5 mM, 7 mM, 7.5 mM, 8 mM, 8.5 mM, 9 mM, 9.5 mM, or 10 mM).

Antibodies

This document also provides methods and materials for obtaining antibodies specific for one or more hapten-polypeptide conjugates. For example, an immunogenic composition comprising hapten-polypeptide conjugates can be prepared as described above and then used to immunize an animal. Various host animals including, for example, rabbits, chickens, mice, guinea pigs, goats, and rats, can be immunized by injection of an immunogenic composition comprising hapten-polypeptide conjugates. For example, polyclonal antibodies with specificity for a particular hapten-polypeptide conjugate can be prepared by injecting the selected immunogenic composition into the host species (e.g., rabbit). In some cases, repeated booster injections of the selected conjugate are provided until high antibody titers are achieved. Depending on the host species, adjuvants can be used to increase the immunological response and include Freund's adjuvant (complete and/or incomplete), mineral gels such as aluminum hydroxide, surface-active substances such as lysolecithin, pluronic polyols, polyanions, peptides, or oil emulsions. Polyclonal antibodies are contained in the sera of the immunized animals. Monoclonal antibodies can be prepared using standard hybridoma technology. In particular, monoclonal antibodies can be obtained by any technique that provides for the production of antibody molecules by continuous cell lines in culture as described, for example, by Kohler et al., *Nature* 256:495-497 (1975); the human B-cell hybridoma technique of Kosbor et al., *Immunology Today* 4:72 (1983); and Cote et al., *Proc. Natl. Acad. Sci. USA* 80:2026-2030 (1983); and the EBV-hybridoma technique of Cole et al., *Monoclonal Antibodies and Cancer Therapy*, Alan R. Liss, Inc. pp. 77-96 (1983). Such antibodies can be of any immunoglobulin class including IgM and IgG, and any subclass thereof. The hybridoma producing the monoclonal antibodies of the invention can be cultivated in vitro or in vivo. Chimeric antibodies can be produced through standard techniques.

In general, antibodies can be isolated from serum by any appropriate method including, without limitation, affinity chromatography, immunoprecipitation, size exclusion chromatography, and ion exchange chromatography, or as described herein. See, for example, Flohe et al., *Biochim. Biophys. Acta.* 220:469-476 (1970), or Tilgmann et al., *FEBS* 264:95-99 (1990). The antibodies provided herein can be substantially pure. The term "substantially pure" as used herein with reference to an antibody means the antibody is substantially free of other polypeptides, lipids, carbohydrates, and nucleic acid with which it is naturally associated in nature. Thus, a substantially pure antibody is any antibody that is removed from its natural environment and is at least 60 percent pure. A substantially pure antibody can be at least about 65, 70, 75, 80, 85, 90, 95, or 99 percent pure.

Antibody populations obtained by the methods provided herein can be subjected to a variety of insoluble matrices (e.g., affinity columns) to increase affinity and/or specificity of the resultant antibody population. To purify polyclonal antibody populations having increased specificity and/or affinity for one or more hapten-polypeptide conjugates, serum from an animal immunized with immunogenic compositions described herein can be subjected to affinity columns with conjugated homologous hapten. In some cases, serum can be depleted of antibodies having affinity for unconjugated hapten using a hapten affinity column (unconjugated hapten affinity column). In some cases, serum can retain antibodies having affinity for a particular chemical moiety, such as an aldol formation, on the polypeptide and/or having affinity for conjugates of the polypeptide and conjugation reagent (referred to alternatively herein as Polypeptide-CL species; polypeptide-crosslinker species; polypeptide-conjugation reagent species) and/or conjugates of the conjugation reagent. Depletion of antibodies reactive with such chemical moieties such as with polypeptide-CL species and/or conjugates of the conjugation reagent can be achieved by passing serum over an affinity resin coupled to the appropriate species, e.g., homologous polypeptide treated with the conjugation reagent; or conjugation reagent. The extent of purification can be measured by any appropriate method including, without limitation, ELISA, radioimmunoassay, immunofluorescence analysis.

Once produced, populations of polyclonal antibodies can be assayed for recognition of a conjugated hapten provided herein by standard immunoassay methods including ELISA techniques, radioimmunoassays, immunofluorescence, immunohistochemistry, and Western blotting. See, *Short Protocols in Molecular Biology, Chapter* 11, Green Publishing Associates and John Wiley & Sons, Edited by Ausubel, F. M et al., 1992. In some cases, antibodies provided herein can exhibit increased affinity and/or specificity to a particular conjugated hapten relative to an unconjugated hapten.

Antibodies prepared according to the methods provided herein can be specific to a particular conjugated hapten. Antibody specificity refers to the degree to which an antibody can differentiate and discriminate between homologous and heterologous conjugated haptens. As used herein, antibodies are said to be "specifically binding" if they do not significantly cross-react with different hapten-conjugate molecules. Antibody specificity can be determined by evaluating cross-reactivity of population of polyclonal antibodies to different conjugated haptens. As demonstrated in Tables 1-5, for example, cross-reactivity can be expressed as the ratio of the concentration of test hapten-conjugate to the concentration of subject hapten-conjugate to achieve the same response. For example, a cross-reactivity of 1:200 ratio conveys that a 200 fold increase in concentration of the different conjugated hapten is necessary to achieve the same response as the conjugated hapten of interest under the same conditions. As used herein, an antibody is said to specifically bind a conjugated hapten of interest if it exhibits greater than a 1:20 (e.g., greater than 1:100, 1:200, 1:500, 1:1000, 1:5000, 1:10,000, or higher) cross-reactivity to at least one different conjugated hapten (e.g., at least two, at least three, at least four, at least five, or more, different conjugated haptens). In some embodiments, the different conjugated hapten is in the same biochemical pathway as the hapten of interest. In some embodiments, the different conjugated hapten is a derivative, metabolite, or precursor to the hapten of interest.

In some cases, an antibody's cross-reactivity with related haptens, e.g., haptens derived from the same biochemical pathway or metabolites, precursors, or derivatives of the hapten of interest, can be assayed. For example, dopamine is the precursor for norepinephrine, while norepinephrine is the precursor of epinephrine and metabolites such as Catechol-Methyl Transferase products (COMT) of dopamine (3-methoxy-tyramine), norepinephrine (meta-norepinephrine) and epinephrine (metanephrine). An example of a cross-reactivity study is the following: an antibody to conjugated dopamine should be specific to dopamine and should not react, or have very limited reactivity, with its precursor tyrosine and/or L-DOPA, norepinephrine, or 3-methoxy-tyramine (COMT product of dopamine). As described herein, polyclonal antibodies against BSA-conjugated DOPAC demonstrate greater than 1:10,000 cross-reactivity with antibodies against BSA-conjugated dopamine, norepinephrine, and tyramine. Accordingly, a 10.000-fold increase in the concentration of the related hapten conjugate (e.g., dopamine, norepinephrine, or tyramine conjugate) is necessary to achieve the same response as the hapten of interest under the same conditions. Non-fractionated affinity purified antibodies against dopamine and norepinephrine display low but detectable cross-reactivity to each other (1:40 and 1:47, respectively). Accordingly, a 40-fold increase in conjugated norepinephrine is necessary to achieve a response comparable to that of conjugated dopamine.

Polyclonal antibodies specific to stereoisomers of epinephrine, L-theanine, tyramine, tryptamine, agmatine and 6-sulfatoxy-melatonin conjugated to carrier proteins (BSA) are also provided herein. The antibodies were prepared by the methods described herein. For example, the one-step conjugation reaction for preparing immunogen was used to induce and obtain isolated polyclonal antibodies specific to agmatine, tyramine, tryptamine, 6-sulfatoxy-melatonin and L-theanine with a low ratio of hapten to polypeptide. The two-step conjugation reaction for preparing immunogen was used to induce and obtain isolated antibodies specific to the stereoisomers of epinephrine.

Methods of Using Antibodies

This document provides methods for detecting, determining, and measuring the presence of one or more haptens in a biological sample using the antibodies provided herein. In some cases, the biological sample is treated according to a one-step or two-step conjugation reaction (e.g., to generate a conjugate-hapten species for detection by the antibody) prior to immunoassays with such antibodies.

Biological samples can include, without limitation, urine, blood, serum, platelets, cerebrospinal fluid (CSF), and saliva. Any appropriate method can be used to obtain a biological sample from a mammal (e.g., a human subject). For example, a blood sample can be obtained by peripheral venipuncture or finger stick, saliva and urine samples can be obtained using standard urine collection techniques, and cerebrospinal fluid can be obtained via a lumbar puncture. A sample can be in a variety of physical states, e.g., liquid, solid, emulsion, or gel. Samples can be treated to preserve the integrity of biological samples. Such treatment can include the use of appropriate buffers and/or inhibitors, such as inhibitors of certain biological enzymes and bacterial activity. One having ordinary skill in the art will be able to determine the appropriate conditions given the hapten of interest and the nature of the sample. A sample can be manipulated prior to being evaluated for the level of one or more haptens. For example, a sample can be concentrated, dried, diluted, lyophilized, extracted, fractionated, subjected to chromatography, purified, acidified, reduced, degraded, subjected to enzymatic treatment, or otherwise treated in ways known to those having ordinary skill in the art in order to facilitate detection of the hapten of interest. If desired, a sample can be a combination (e.g., pool) of samples, e.g., from an individual. In some cases, samples can be obtained from an individual at different points of time (e.g., prior to administering a medicament or other therapeutic regimen and after administering a medicament or other therapeutic regimen).

Biological samples can be prepared by contacting the sample with a conjugation reagent according to a two-step or one-step conjugation reaction. In the two-step reaction, a biological sample is contacted with a polypeptide or fragment thereof (e.g., BSA, TG, OVA, or gelatin) which has been separately treated with a conjugation reagent (e.g., a pretreated polypeptide). Upon contacting the biological sample with separately treated polypeptide, haptens present in the biological sample can bind to the conjugation moiety on the treated polypeptide, as described previously for the preparation of the immunogenic compositions. In this manner, contacting the treated polypeptide to the biological sample can promote in situ formation of hapten-polypeptide conjugates. According to the one-step conjugation method, one or more conjugation reagents can be contacted to a biological sample or clinical test solution in order to form conjugates between endogenous polypeptides (or exogenous polypeptides added to the sample) and any amine-containing hapten also present in the sample. Following either the two-step or the one-step preparation method, haptens converted in situ into hapten-polypeptide conjugates can be immunologically assayed using the purified conjugated hapten-specific antibodies described previously.

Any appropriate method for detecting the presence of conjugated hapten in a biological sample can be used. In some cases, the detection method can be a competitive ELISA in which known concentrations of a homologous hapten conjugated to a heterologous carrier protein and the corresponding hapten-specific antibody compete with an unknown amount of in situ conjugated haptens in a biological sample. In some cases, the assays are done in solution. In other cases, a solid substrate is used. For example, homologous hapten-heterologous polypeptide conjugates can be immobilized on a solid substrate by any of a variety of methods known in the art and then exposed to the hapten-specific antibody and a biological sample prepared as described herein. If hapten-polypeptide conjugates are present in the prepared biological sample, the hapten-specific antibody can bind the conjugates. In some cases, the hapten-specific antibody can be covalently linked to an enzyme (e.g., alkaline phosphatase, horseradish peroxidase), or can be detected using a secondary antibody conjugated to an enzyme. A standard curve can be developed using serial dilutions of conjugates comprising homologous hapten and heterologous polypeptide (e.g., any polypeptide other than then the polypeptide used for immunization) in an appropriate solution.

In some cases, levels of conjugated haptens can be measured using an immunoassay (e.g., a competitive enzyme-linked immunosorbent assay (ELISA), Western blot, "sandwich" non-competitive immunoassay). In an immunological assay, an antibody having specific binding affinity for a hapten of interest or a secondary antibody that binds to such an antibody can be detectably labeled, either directly or indirectly. A "detectable label" as used herein refers to a detectable compound or composition which is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition which is detectable. Suitable labels include, without limitation, radionuclides (e.g., $^{125}$I, $^{131}$I, $^{35}$S, $^{3}$H, $^{32}$P, $^{33}$P, or $^{14}$C), fluorescent moieties (e.g., fluorescein, FITC, APC, PerCP, rhodamine, or PE), luminescent moieties (e.g., QDOT™ nanoparticles supplied by the Quantum Dot Corporation, Palo Alto, Calif.), compounds that absorb light of a defined wavelength, or enzymes (e.g., alkaline phosphatase or horseradish peroxidase). Antibodies can be indirectly labeled by conjugation with biotin then detected with avidin or streptavidin labeled with a molecule described above. Methods of quantifying a label depend on the nature of the label and are known in the art. Examples of detectors include, without limitation, x-ray film, radioactivity counters, scintillation counters, spectrophotometers, colorimeters, fluorometers, luminometers, and densitometers. Combinations of these approaches (including "multi-layer" assays) familiar to those in the art can be used to enhance the sensitivity of assays.

Appropriate solid substrates to which homologous haptens-heterologous carrier protein conjugates can be bound include, without limitation, microtiter plates (e.g., polystyrene or polyvinylchloride microtiter plates), tubes, membranes such as nylon or nitrocellulose membranes, and beads or particles (e.g., agarose, cellulose, glass, polystyrene, polyacrylamide, magnetic, or magnetizable beads or particles). Any appropriate method can be used to immobilize conjugates to a solid support. Immobilization of the biological sample can be non-specific (e.g., adsorption to a solid support) or specific (e.g., capture by another antibody specific to the sample antigen).

Articles of Manufacture

This document also provides methods and materials for providing the hapten-specific antibodies described herein as articles of manufacture (e.g., kits) containing packaging material, a hapten-specific antibody within the packaging material, and a label that indicates that the hapten-specific antibody or composition is useful for detecting a hapten in a biological sample.

The articles of manufacture provided herein also can comprise one or more detectable labels. For example, an article of manufacture can be a kit comprising a hapten-specific antibody and reagents to add a detectable label to the antibody. Suitable labels to be provided in such a kit can include, without limitation, radionuclides (e.g., $^{125}$I, $^{131}$I, $^{35}$S, $^{3}$H, $^{32}$P, $^{33}$P, or $^{14}$C), fluorescent moieties (e.g., fluorescein, FITC, APC, PerCP, rhodamine, or PE), luminescent moieties (e.g., QDOT™ nanoparticles supplied by the Quantum Dot Corporation, Palo Alto, Calif.), compounds that absorb light of a defined wavelength, or enzymes (e.g., alkaline phosphatase or horseradish peroxidase).

In some cases, the articles of manufacture provided herein also can comprise a conjugation reagent. For example, an article of manufacture can be a kit comprising a hapten-specific antibody, a conjugation reagent (e.g., the conjugation reagent used to prepare the hapten-specific antibody), and a label that indicates that the conjugation reagent is useful for preparing a biological sample and/or for making additional immunogenic compositions. In other cases, an article of manufacture can be a kit comprising a hapten-specific antibody, a conjugation reagent, reagents for performing an immunoassay, and a label that indicates that reagents provided in the kit are useful for preparing a biological sample and detecting and quantifying a hapten of interest if present in the sample. For example, an article of manufacture can include reagents such as secondary antibodies, sterile water, pharmaceutical carriers, buffers, indicator molecules, solid substrates (e.g., beads, microtiter plate), and/or other useful reagents for using hapten-specific antibodies to detect the presence or absence of a hapten of interest in a biological sample. In some cases, hapten-specific antibodies, detectable label, and/or other reagents can be provided in a container, such as a plastic, polyethylene, polypropylene, ethylene, or propylene vessel that is either a capped tube or a bottle. Alternatively, hapten-specific antibodies can be included on solid substrates such as beads or microtiter plates.

The articles of manufacture provided herein contain packaging materials. Packaging materials for use in packaging pharmaceutical products are well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The invention will be further described in the following examples, which do not limit the scope of the invention described in the claims.

EXAMPLES

Example 1

Preparing Immunogens Using Amine-Containing Haptens

Amine-containing neurotransmitters and biogenic amines (collectively referred to as "haptens") were coupled to carrier proteins (CP): bovine sera albumin (BSA), thyroglobuline (TG), keyhole limpet hemocyanin (KLH), or ovalbumin (OVA) using glutaric aldehyde. For BSA, TG, and OVA carrier proteins, cross-linking was performed in 100 mM Na-phosphate buffer, pH 7.5, or in 50 mM sodium carbonate/bicarbonate buffer, pH 9.2-9.6, supplemented with 500 mM NaCl. Cross-linking with KLH was performed likewise but in the presence of 1.0 M NaCl throughout the whole procedure. The polypeptide:hapten ratio was 10:1 (w/w) (or on average 1 mM hapten per 1 mM lysine in the polypeptide carrier protein (e.g., KLH, BSA, OVA, thyroglobuline). The final glutaric aldehyde concentration was between 5-10 mM. Incubation times varied between 30 minutes and 6 hours at room temperature. Schiff's bases were reduced with a final concentration basis of 30 mM NaCNBH$_3$. Unbound haptens, free glutaric aldehyde, small polymers of glutaric aldehyde and haptens were removed from the solution through 6000-8000 MWCO dialysis against a 10 mM phosphate buffer (pH 7.5) with 500 mM NaCl, or with 1.0 M NaCl for KLH conjugates. Fine tuning to optimal incorporation of haptens were achieved by using either pH 7.5 or 9.2, or small variations in glutaric aldehyde concentrations and CP:hapten (w/w) ratio from 10:1 to 10:0.1.

Incorporation of haptens into CP was followed by spectrophotometric analyses, IEF and SDS-PAGE, if appropriate. Optimal CP-hapten immunogen was also assessed in a competitive ELISA with hapten-specific antibodies using haptens coupled to different carrier proteins. All immunogens were stored at final concentrations of 500 µg CP/mL with 0.02% NaN$_3$ at −20° C.; except for KLH immunogens which were stored at 4° C.

Example 2

Preparing Immunogens of Non-Amine-Containing Hapten-Carrier Protein Conjugates

Non-amine containing haptens (5-HIAA, DOPAC, DHPG, and melatonin) were conjugated to carrier proteins through a Mannich condensation reaction. Hapten condensations were performed with a 3.5% final concentration of formaldehyde (with 10% methanol to prevent polymerization) in 0.25 M MES buffer, pH 5.5, containing 500 mM NaCl, 2 mM Vitamin C, and incubated for 24-48 hours at 37° C. with protection from light. Unbound haptens, free formaldehyde, and other small fragments were removed by excessive dialysis through a 6000-8000 MWCO modified cellulose membrane (Spectro/Por, Spectrumlabs) against a 10 mM sodium hydrogen carbonate buffer, pH 8.0, with 0.5M NaCl. Fine tuning of the conjugated haptens were performed with slight modifications of carrier protein-hapten (w/w) ratio and incubation times, as monitored by spectrophotometric analysis, SDS-PAGE, IEF, if appropriate, and reactivity to hapten specific antibody.

Example 3

Immunization and Antibody Isolation and Purification

Immunization protocols were conducted at SynBioSci (Livermore, Calif.) or Maine Biotechnology Service (Portland, Me.). New Zealand White rabbits were primed with 1 mL of hapten-conjugate containing, on average, 50 µg of hapten coupled to 500 µg carrier protein. The immunogen was mixed with 1 mL of Freund's complete adjuvant immediately prior to injection. The injections were done subcutaneously in 8-10 sites on the flank and thorax of the rabbits. Booster injections were administered every 2 weeks and consisted of 1 mL of hapten conjugate containing on average 50 µg of hapten coupled to 500 µg carrier protein and mixed with 1 mL of Freund's incomplete adjuvant immediately prior to injection. Serum was obtained one week after each booster for analysis of antibody specificity and titer. A typical protocol lasted 69 days, and resulted in six sequential bleeds before the rabbits were exsanguinated. Prolonged immunizations were performed for successful immunizations, using at least two additional boosters every two weeks, before termination.

Based on the specificity and titer of the anti-hapten antibodies in whole serum, it was determined whether further purification was necessary. If the whole serum exhibited cross-reactivity towards the homologous hapten and related molecules, an affinity isolation was performed. If the whole serum exhibited reactivity only towards the homologous hapten and carrier protein, an anti-carrier protein antibody depletion was performed. Hapten affinity columns were prepared using AminoLink® Immobilization Kits (Pierce, Rockford, Ill.) according to a modified protocol. Two milliliters of AminoLink® Coupling Resin were added to a 10 mL gravity column and equilibrated with a 0.1 M sodium borate buffer, pH 8.0, (Gentle Ag/Ab Binding Buffer, Pierce, Rockford, Ill.). Ten milligrams of hapten were dissolved in 3 mL of sodium borate buffer and added to the column with 50 mM NaCNBH3. Columns were incubated in the dark with continuous rocking at room temperature for six hours. Columns were washed with excess 1.0 M Tris-HCl, pH 7.5, containing 150 mM NaCl and quenched by incubating 3 mL of 1.0 M Tris, pH 7.5, 50 mM NaCNBH3 for 30 minutes at room temperature with constant rocking.

Antibodies were isolated from serum on a hapten affinity column according to the following protocol. Columns were equilibrated with excess sodium borate buffer. Delipidized serum was diluted 1:2 in sodium borate buffer and incubated on the column for 2 hours at room temperature and protection from light with constant rocking. After incubation, the columns were washed with an excess of PBS until A$_{280}$ nm was <0.025. Antibodies were eluted with 0.1 M Glycin-HCl 250 mM NaCl, pH 2.4 and immediately brought to pH 7 with Tris. Antibody solutions were dialyzed overnight against PBS. If appropriate, antibodies were isolated using a pH gradient from pH 6.0-2.4, in order to characterize antibody subpopulations with different specificities and affinity.

Carrier protein AminoLink® affinity columns were prepared as follows. A suboptimal final concentration of 80 mM glutaric aldehyde was added to 10 mg of carrier protein in 3 mL 0.1 M phosphate buffered saline (BupHTM Phosphate Buffered Saline Pierce, Rockford, Ill.). The carrier protein-aldehyde solution was allowed to incubate in the dark at room temperature for 60 minutes. One milliliter of 1.9 M Ethanolamine, pH 9.0, was added and the solution was incubated in dark at room temperature for 45 minutes. NaCNBH$_3$ was added to a final concentration of 50 mM. After an incubation of 15 minutes, the conjugate solution was then dialyzed extensively against 10 mM borate buffer, pH 8.0, overnight at 4° C. The cross-linker treated BSA (CP-CL) was bound to AminoLink® coupling resin according to the protocol above. Carrier protein columns for antibodies raised against haptens coupled by the Mannich condensation reaction were prepared using a PharmaLink® Immobilization Kit (Pierce, Rockford, Ill.) according to a modified protocol. A PharmaLink® affinity column containing diaminodipropylamine coupled to 2 mL of agarose beads was equilibrated with 0.1 M MES, 0.15 M NaCl, pH 4.7. Ten milligrams of BSA was dissolved in 4 mL of 0.1 M MES, 0.15 M NaCl, pH 4.7, and formaldehyde was added to final concentration of 10%. Columns were incubated overnight at 37° C. with constant rocking. Columns were washed with an excess of 0.1 M Tris, pH 7.5.

Anti-carrier protein antibodies were removed according to the following protocol. Columns were equilibrated with sodium borate buffer. Serum was diluted 1:2 in sodium borate buffer and incubated on the column for 1 hour at room temperature with constant rocking. The flow-through of depleted serum was collected and anti-carrier protein antibodies were eluted with 0.1 M glycine, pH 1.5, and immediately neutralized with Tris. This process was repeated 2-3 times, depending on the efficiency of the depletion of anti-carrier protein antibodies. Complete depletion of anti-carrier protein antibodies was assessed by ELISA.

Polyclonal antibodies to the following eighteen haptens were generated: L-theanine, epinephrine, agmatine, glutamate, glutamine, GABA, glycin, tyramine, dopamine, DOPAC, norepinephrine, tryptamine, serotonin, 5-HIAA, melatonin, histamine, taurine, and β-PEA.

Example 4

Antibody Characterization and Quantification

Glutaric aldehyde conjugates for cross-reactivity studies were made essentially according the procedure as described for immunogens, but only with BSA, TG, or gelatin as carrier proteins. Hapten-conjugates for cross-reactivity studies include haptens close but not similar as the original hapten. They are chemically modified molecules, precursors, derivatives, metabolites of the original hapten. After terminating the cross-linking reaction, unsaturated aldehyde groups were quenched with excess Tris (hydroxymethyl)aminomethane (Tris-HCl, pH 7.5) at a final concentration of 10 mM. After dialysis in 10 mM Tris-HCl, pH 7.5, 500 mM NaCl, the conjugated haptens were formulated to 1.0 mg CP/mL in 50% glycerol and 0.02% sodium azide and stored at −20° C. The formaldehyde Mannich condensation reaction conjugates were made essentially as described above, but only with BSA and OVA as carrier proteins. The reaction was stopped by dialysis against 10 mM Tris-HCl pH 7.5, 500 mM NaCl. The MCR-conjugated haptens were formulated to 1.0 mg carrier protein/mL in 50% glycerol and 0.02% sodium azide and stored at −20° C. A competitive ELISA was created for each anti-hapten antibody. Polystyrene 96-well flat-bottom immunoassay plates (Nalgene Nunc International, Rochester, N.Y.) were coated overnight at room temperature and protected from light with the corresponding hapten conjugate in coating buffer (50 mM sodium carbonate-bicarbonate, pH 9.2-9.6) at a concentration optimized for each assay (usually between 1-5 µg/mL). Plates were washed 6 times with 250 µL/well of wash buffer (5 mM phosphate buffer pH 7.5, 50 mM NaCl, 0.002% TWEEN® 20 nonionic detergent) using a Tecan 96 PW™ plate washer (Tecan Trading AG, Männedorf, Switzerland). This washing protocol was used after each incubation step. The plates were blocked with StabilGuard® biomolecule stabilizer (SurModics, Inc.) for at least 20 minutes. Standards were made by a serial dilution of homologous hapten conjugates to a heterologous CP in 10 mM sodium phosphate buffer, pH 7.2, containing 150 mM NaCl (PBS), 10% StabilZyme Select® stabilizer (SurModics, Inc.), 0.1% BSA, and 0.1% TWEEN® 20 nonionic detergent. Standards and competitors (75 µL) were incubated along with (75 µL) optimized concentration of hapten-specific antibody in PBS, 0.1% BSA, and 0.1% TWEEN® 20) overnight at 32° C. with constant shaking. Plates were then incubated with 150 µL/well of secondary antibody, goat-anti-rabbit IgG-alkaline phosphatase, in PBS, 0.1% BSA, 0.5% normal goat serum, 0.1% TWEEN® 20, for 1 hour with constant shaking at room temperature at optimized concentrations. Finally, to each well was added 150 µL of alkaline phosphatase substrate buffer containing 2.5 mM p-nitrophenyl phosphate disodium hexahydrate in 1 M diethanolamine, pH 9.5. Absorbance at 405 nm was obtained using a SUNRISE™ plate reader (Tecan, Männedorf, Switzerland).

Longitudinal serum bleeds were tested in a direct-ELISA with serial dilutions on coated plates with the original immunogen and the homologous hapten conjugated to a heterologous CP. The coating of antigens, incubation time, washing of the plates, secondary antibody and substrate development were as described before.

Antibody specificity was determined using the competitive ELISA and the results were the average of four independent observations. A standard titration of the conjugated hapten was prepared by serially diluting the 1 mg/mL carrier protein in PBS, 0.1% BSA, and 0.1% TWEEN® 20 and run in the ELISA under the above protocol. The related hapten conjugates were titrated under identical conditions and compared to the standard curve generated. The concentration of the hapten conjugate was plotted against the absorbance values obtained from the ELISA in a semi-log plot. The linear-regression tool of the EXCEL® spreadsheet program (Microsoft, Seattle, Wash.) was used to find an equation for the linear region of the concentration-absorbance curve of the homologous hapten. Observed concentrations for the related hapten conjugates were calculated from this equation using absorbance values which fell in the linear region of the standard curve. Cross-reactivity was expressed as the average ratio of observed concentration to actual concentration in relation to the homologous hapten. The results of cross-reactivity studies are the average of at least four independent experiments.

Example 5

Preparing Clinical Samples

Urine

Clinical urine specimens can be prepared as follows. One-step-procedure: A clinical acidic urine sample (equivalent 1.0 creatinin or 40 gms/dL) is neutralized to pH 8.0 with 1.0 M NaHCO3, containing 0.1% TRITON® X-100 nonionic detergent. A calculated amount of glutaric aldehyde of 66 mM final is added to the sample and the sample is incubated at room temperature for one to three hours, depending on the assay type, to form neurotransmitter or biogenic amine conjugates/aggregates. Excess glutaric aldehyde is quenched with a mixture of amino-group-containing compounds (e.g., diethanolamine and Tris-HCl, pH 7.5). The reaction mixture is formulated finally with in the appropriate buffer for enzyme immunoassay (EIA) analyses, containing BSA, gelatin, TRITON® X-100, and phosphate buffered saline (PBS), pH 7.5.

Alternatively, urine specimens can be prepared as follows. Two-step-procedure:. Gelatin or BSA (whole polypeptides or fragments thereof) solution is prepared to 10 mg/mL in 100 mM phosphate buffer (pH 7.5) containing 150 mM NaCl. The solutions are allowed to react with a final concentration of 0.5 M glutaric aldehyde during a 24-hour incubation at room temperature with constant stirring and protection from light. Excess glutaric aldehyde is removed by excessive dialysis against PBS or by gel filtration on G25 Sephadex beads. 100 µL of the pre-treated Gelatin or BSA conjugate is added to a clinical specimen (see before or after neutralization with $NaHCO_3$) and allowed to react with the analytes in the clinical solution while incubating for 2-24 hours. The sample is quenched with a mixture of amine-containing-compounds (e.g., diethanolamine and Tris-HCl, pH 7.5). The reaction mixture is formulated with the appropriate buffer for enzyme immunoassay (EIA) analyses, containing BSA, gelatin, TRITON® X-100, and phosphate-buffered saline, pH 7.5. The samples can be tested as described hereafter or stored at −20° C.

Semi-quantitative neurotransmitter-biogenic enzyme immunoassay (EIA) is performed. The assay follows a competitive ELISA format, in which a fixed amount of a conjugated neurotransmitter and biogenic amine specific antibody competes with an unknown amount of the homologous in situ conjugated neurotransmitters and biogenic amines in the sample as described above, and a constant amount of the conjugated neurotransmitter or biogenic amines coated to the solid phase. In this EIA format, the amount of antibody bound to the solid phase is inversely related to the amount of conjugated analyte in the test sample. The amount of bound rabbit antibody is determined by means of a goat antibody tagged with alkaline phosphatase (AP) and specific for a rabbit IgG. The color development of the AP-substrate is monitored at 405 nm, the intensity is proportional to the amount of bound rabbit IgG. For each neurotransmitter analysis, a calibration curve is performed in parallel. Both calibration and coating reagent in a neurotransmitter/biogenic amine assay of interest is prepared by means of covalently coupling of the neurotransmitter/biogenic amine to a carrier protein distinct from the carrier protein used to prepare the immunogen. For example, porcine thyroglobulin, BSA, or ovalbumin can be used.

Saliva

To prepare saliva samples, approximately 500 µL saliva is freeze-thawed three times and centrifuged at 3000 rpm for 5 minutes at 8° C. 100 µL of each sample is placed in a bullet vial for cross-linking and 100 µL of sample is placed in a bullet for a non-cross-linked sample (control). 50 µL of 6M urea and 50 µL of PBS containing sodium azide and 0.1% TRITON®X-100 are added to all tubes. The tubes are incubated for at least 5 minutes while vortexing. 100 µL of 1X PBS are added to the non-cross-linked sample and the lid is closed. While vortexing, 4×25 µL glutaraldehyde solution (100 mM final) are slowly added. All tubes are incubated for 60 minutes at room temperature with protection from light. 200 µL of the quenching buffer is added (see urine sampling above) to each tube and mixed well. The tubes incubate for about 30 minutes at room temperature. The samples may be tested immediately in the ELISA as described for urine (see above), or frozen and stored at −20° C. for later testing. For testing, each saliva sample is diluted 1:1 with the antibody preparation. Samples value are corrected with the values obtained from the non-cross linked samples. Saliva samples can also be de-proteinated prior to analysis, to reduced matrix effect (non-specific background signals). The procedure is essentially as described for plasma and serum (see below).

Serum or Plasma

To prepare serum or plasma samples, proteins are precipitated with cold trichloric acid (TCA) to a final concentration of 5%. Precipitated proteins are removed by centrifugation at 10,000×g. The acidic supernatant is neutralized with saturated KOH solution. Equal aliquots for cross-linked and non-cross-linked samples are prepared. 100 mM sodium phosphate buffer is added to a final volume of 200 µL. The samples are incubated with 100 µL glutaric aldehyde to 100 mM final concentration. To the non-crosslinked samples, 100 µL 1X PBS is added. All tubes are incubated for 1-2 hours at room temperature in the dark. 200 µL of quenching buffer is added to the tubes and mixed well. The tubes incubate for about 30 minutes at room temperature. The samples may be tested immediately in the ELISA, or frozen and stored at −20° C. for later testing. For each assay, serum samples (cross-linked and non-cross-linked) are diluted 1:1 with the antibody preparation. Samples values are corrected with the values obtained from the non-cross linked samples.

Example 6

Glycine Immunological Assay

To test the specificity of glycine-specific antibodies, forty urine test samples were prepared as described in Example 5. Glycine was assayed for under the following conditions. A constant amount of the conjugated thyroglobulin-glycine (TG-glycine) was coated to the solid phase. Twelve urine samples prepared as described above. The antibody was affinity purified-IgG-glycine (diluted 1:800), and the antibody detection was by goat anti-rabbit-IgG-AP (diluted 1:15,000). The color development of the AP-substrate was monitored at 405 nm, where the intensity was proportional to the amount of bound rabbit IgG Immunoassay results are presented in FIG. 1.

Figure 2:
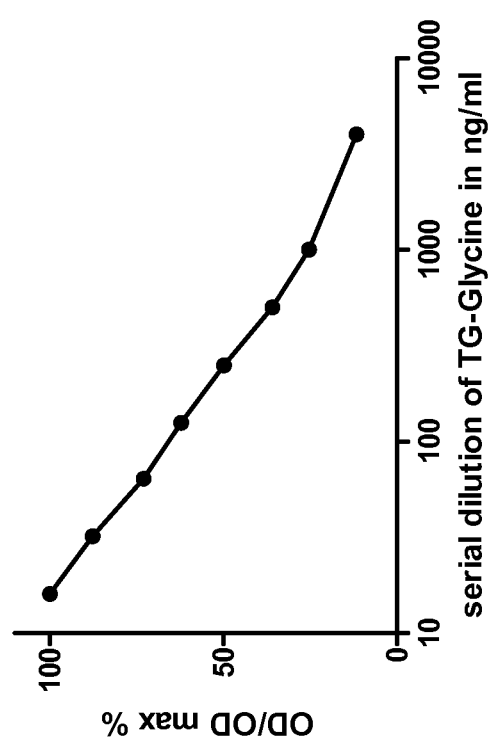
FIG. 2 depicts a standard curve for serial dilutions of TG-glycine conjugates. Wells were coated in TG-glycine (1:800). Primary antibody: IgG-glycine (1:800); secondary antibody: alkaline phosphatase conjugate (GR-AP) (1:15,000).
Figure 3:
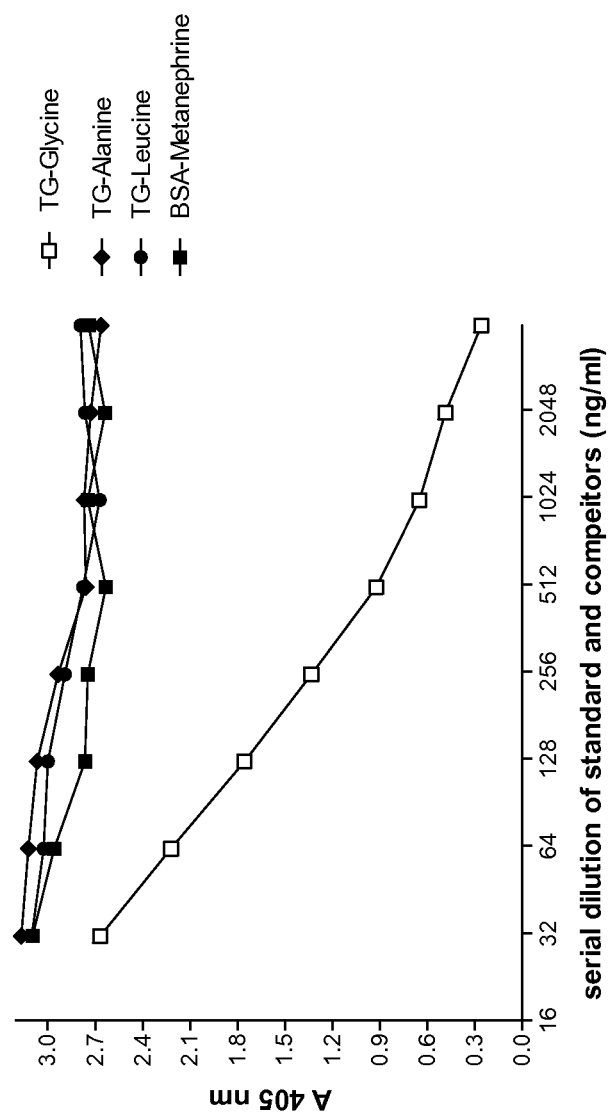
FIG. 3 depicts cross-reactivity of the conjugated glycine-specific antibody Aff-IgG-glycine to related biologically active small molecules: TG-glycine; TG-alanine; TG-leucine; and BSA-metanephrine.
Figure 4:
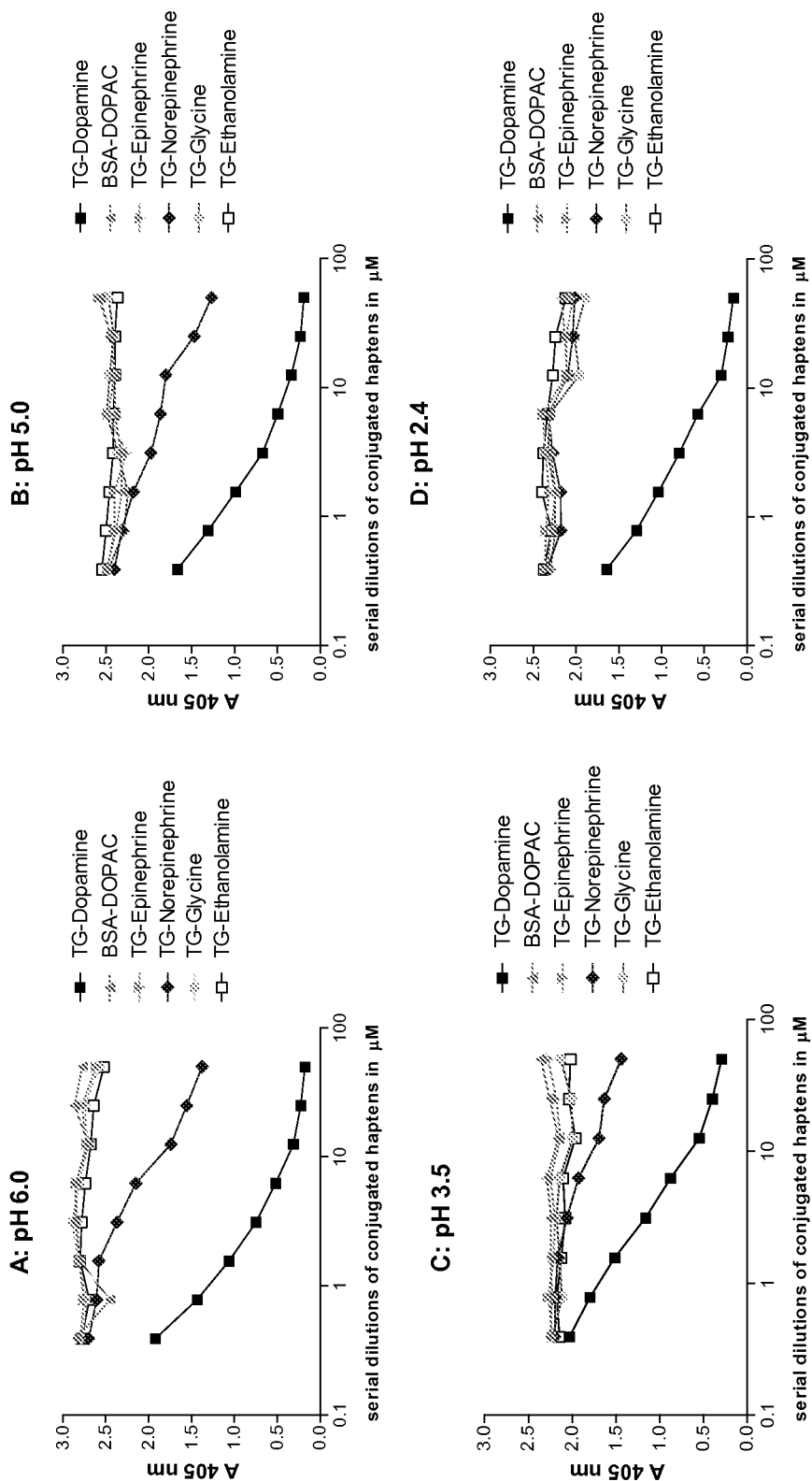
FIGS. 4A-D depict a comparison of the specificity of anti-dopamine antibodies isolated by affinity chromatography and pH gradient. Anti-dopamine antibodies were bound to a column of dopamine-conjugated AminoLink beads (Pierce Rockford Ill., USA) and eluted consecutively with a pH gradient of pH 6.0 (A), 5.0 (B), 3.5 (C), and 2.4 (D). Reaction was measured against conjugated dopamine, DOPAC, epinephrine, norepinephrine, and glycine.

As demonstrated in FIG. 2, a calibration curve was prepared for TG-glycine conjugates. The following reaction conditions were used: wells were coated in TG-glycine (1:800); the primary antibody was affinity purified IgG-glycine (1:800); the secondary antibody was alkaline phosphatase conjugate (GR-AP) (1:15,000). Antibody detection was performed using a goat-anti-rabbit antibody conjugated to alkaline phosphatase. The substrate was developed and detected at 405 nm. Alternatively, serial dilutions of glycine are conjugated in situ with glutaric aldehyde in the presence of a constant amount of a carrier protein. After one hour incubation the reaction mixture is quenched with excess Tris and the serial dilution of conjugated glycin is used as calibration curve Cross-reactivity of the glycine-specific antibody with related conjugated amino acids (competitors) was assayed under the following conditions: serial dilutions of thyroglobulin-glycine (TG glycine) were used to coat the wells. The glycine-specific antibody was affinity-purified IgG-anti-glycine and detected with goat anti-rabbit IgG secondary antibody conjugated with alkaline phosphatase. Color development of the AP-substrate was monitored at 405 nm. The competitors and results are set forth in FIG. 3.

Example 7

Hapten-Specific Antibodies

Tables 1-5 summarize the cross-reactivity of purified antibodies raised against conjugated tryptamine, tyramine, L-theanine, agmatine, and epinephrine (cross-reactivity of 6-sulfatoxy-melatonin is not depicted) with charged amino acids, related chemical structures, pharmaceuticals antagonists, and agonists. Antibody specificity was calculated by comparing the observed concentration with the actual concentration. None of the antibodies reacted with free haptens. Antibodies derived from four metabolites of the tryptophan pathway (tryptamine, serotonin, 5-HIAA, and melatonin) were also characterized. All antibodies, once depleted of carrier protein treated with aldehyde (CP-CL), displayed high specificity with no detectable reactivity with other derivatives.

Strong specificity was observed for antibodies derived from the tyrosine pathway (tyramine, dopamine, norepinephrine, DOPAC and epinephrine). Dopamine (3,4-dihydroxyphenylethylamine) differs from norepinephrine (3,4-Dihydroxybenzylalcohol) in a hydroxyl group in the side chain. This difference may be responsible for the difference between the two neurotransmitters in terms of antibody specificity. Cross-reacting antibodies were removed by either carefully dissociating antibodies from a hapten column at a pH gradient or by depletion of antibodies over a norepinephrine column. This resulted in gradual increase of the specificity for dopamine with a simultaneous drop in the overall titer. Antibodies derived from the tyrosine pathway (tyramine, dopamine, DOPAC, and norepinephrine) were also characterized. The DOPAC and tyramine antibody displayed a very high specificity. Non-fractionated affinity purified antibodies against dopamine and norepinephrine displayed a small but detectable cross-reactivity to each other (1:40 and 1:47, respectively). Norepinephrine antibodies displayed 1:263 cross-reactivity to conjugated epinephrine, and low but detectable reactivity against the products of the catechol-ortho-methyltransferase conversion: 1:244. Epinephrine antibody is highly specific with marginal cross-reactivity to norepinephrine. By contrast, antibodies from the tryptophan pathway did not display detectable reactivity to 3-methoxy indole derivatives.

TABLE 1

Cross Reactivity of Tryptamine Antibody with Related Conjugated Competitors

| Competitor | Anti-Tryptamine |
|---|---|
| TG-Tryptophan | >1:10,000 |
| BSA-Tryptamine | 1 |
| BSA-5-HTP | >1:10,000 |
| BSA-5-HT | 1:5,000 |
| BSA-5-HIAA | >1:10,000 |
| BSA-5-HTOL | >1:10,000 |
| BSA-N—Ac-5-HT | >1:10,000 |
| BSA-Melatonin | >1:10,000 | n = 4; % CV = 2.6%-4.8%

TABLE 2

Cross Reactivity of Tyramine Antibody with Related Conjugated Competitors

| Competitor | Anti-Tyramine |
|---|---|
| BSA-Norepinephrine | >1:10,000 |
| BSA-Dopamine | >1:10,000 |
| BSA-Epinephrine | >1:10,000 |
| BSA-Phenylalanine | >1:10,000 |
| BSA-Tyrosine | >1:10,000 |
| BSA-L-DOPA | >1:10,000 |
| BSA-β-PEA | >1:10,000 |
| BSA-Tyramine | 1 |

TABLE 2-continued

Cross Reactivity of Tyramine Antibody with Related Conjugated Competitors

| Competitor | Anti-Tyramine |
|---|---|
| BSA-3-Methoxy-Tyramine | >1:10,000 |
| BSA-Normetanephrine | >1:10,000 |
| BSA-Metanephrine | >1:10,000 |
| BSA-DOPAC | >1:10,000 |
| BSA-DHPG | >1:10,000 | n = 4, % CV = 3.8%-7.9%

TABLE 3

Cross Reactivity of L-Theanine Antibody with Related Conjugated Competitors

| Competitor | Anti-L-Theanine |
|---|---|
| TG-L-Theanine | 1 |
| BSA-Glutamic acid | >1:10,000 |
| BSA-GABA | >1:10,000 |
| BSA-Glutamine | >1:10,000 |
| BSA-β-PEA | >1:10,000 | n = 4; % CV = 2.1%-3.8%

TABLE 4

Cross Reactivity of Agmatine Antibody with Related Conjugated Competitors

| Competitor | Anti-Agmatine |
|---|---|
| OVA-Agmatine | 1 |
| BSA-Glutamic acid | >1:10,000 |
| BSA-Lysine | >1:10,000 |
| BSA-Arginine | >1:10,000 |
| BSA-Cadaverine | >1:10,000 | n = 4; % CV = 1.1%-2.8%

TABLE 5

Cross Reactivity of (+/−)Epinephrine Antibody with Related Conjugated Competitors

| Competitor | Anti-(+/−)Epinephrine |
|---|---|
| (G-)elatin-(+/−)Epinephrine | 1 |
| G-Metanephrine | >1:10,000 |
| G-Norepinephrine | >1:10,000 |
| G-Dopamine | >1:10,000 |
| Gelatin-only | >1:10,000 | n = 4; % CV = 6.1%-8.8%

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for preparing a biological fluid sample for detecting a hapten of interest in a biological fluid sample, wherein said hapten contains at least one of an amine and an active hydrogen atom and wherein said biological fluid sample is a clinical sample selected from the group consisting of blood, plasma, serum, platelets, urine, cerebrospinal fluid, sputum, tears, amniotic fluid, vitreous humor, and saliva, said method comprising the steps of: 1. contacting a conjugation reagent selected from glutaric aldehyde and formaldehyde to said biological fluid sample, whereby said hapten of interest, if present in said biological fluid sample, will conjugate with one or more polypeptides in said biological fluid sample to form one or more polypeptide-hapten conjugates; 2. quenching unreacted conjugation reagent in said biological fluid sample after step 1 with an excess of a quenching reagent to provide a quenched solution comprising said biological fluid sample, wherein said quenching reagent is selected from the group consisting of Tris, ethanolamine, diethanolamine, salts thereof, and mixtures thereof; 3. contacting an antibody specific for the hapten to said quenched solution comprising said biological fluid sample and wherein said antibody is generated from a conjugate of the hapten with an immunogenic carrier protein or fragment thereof conjugated in the presence of said conjugated reagent; 4. determining if said antibody binds to at least one of the one or more polypeptide-hapten conjugates if present in said biological fluid sample using an immunoassay.

2. The method of claim 1, wherein the clinical sample is blood.

3. The method of claim 1, wherein the clinical sample is plasma.

4. The method of claim 3, wherein the clinical sample is protein-free plasma.

5. The method of claim 1, wherein the clinical sample is serum.

6. The method of claim 1, wherein the clinical sample is platelets.

7. The method of claim 1, wherein the clinical sample is urine.

8. The method of claim 1, wherein the clinical sample is cerebrospinal fluid.

9. The method of claim 1, wherein the clinical sample is sputum.

10. The method of claim 1, wherein the clinical sample is tears.

11. The method of claim 1, wherein the clinical sample is amniotic fluid.

12. The method of claim 1, wherein the clinical sample is vitreous humor.

13. The method of claim 1, wherein the clinical sample is saliva.

14. The method of claim 1, wherein the conjugation reagent is glutaric aldehyde.

15. The method of claim 1, wherein the conjugation reagent is formaldehyde.

16. The method of claim 1, wherein the quenching reagent is a mixture of Tris or a salt thereof and ethanolamine.

17. The method of claim 1, wherein the quenching reagent is Tris or a salt thereof.

18. The method of claim 1, wherein the quenching reagent is ethanolamine.

19. A method for preparing a biological fluid sample for detecting a hapten of interest in a biological fluid sample, wherein said hapten contains at least one of an amine and an active hydrogen atom and wherein said biological fluid sample is a clinical sample selected from the group consisting of protein-free plasma, serum, urine, cerebrospinal fluid, sputum, tears, amniotic fluid, vitreous humor, and saliva, said method comprising the steps of: 1. contacting a conjugation reagent selected from glutaric aldehyde and formaldehyde to said biological fluid sample, whereby said hapten of interest, if present in said biological fluid sample, will conjugate with one or more polypeptides in said biological fluid sample to form one or more polypeptide-hapten conjugates; 2. quenching unreacted conjugation reagent in said biological fluid sample after step 1 with an excess of a quenching reagent to provide a quenched solution comprising said biological fluid sample, wherein said quenching reagent is selected from the group consisting of Tris, ethanolamine, diethanolamine, salts thereof, and mixtures thereof; 3. contacting an antibody specific for the hapten to said quenched solution comprising said biological fluid sample and wherein said antibody is generated from a conjugate of the hapten with an immunogenic carrier protein or fragment thereof conjugated in the presence of said conjugated reagent; 4. determining if said antibody binds to at least one of the one or more polypeptide-hapten conjugates if present in said biological fluid sample using an immunoassay.

20. The method of claim 19, wherein the clinical sample is protein-free plasma.

21. The method of claim 19, wherein the clinical sample is serum.

22. The method of claim 19, wherein the clinical sample is urine.

23. The method of claim 19, wherein the clinical sample is cerebrospinal fluid.

24. The method of claim 19, wherein the clinical sample is sputum.

25. The method of claim 19, wherein the clinical sample is tears.

26. The method of claim 19, wherein the clinical sample is amniotic fluid.

27. The method of claim 19, wherein the clinical sample is vitreous humor.

28. The method of claim 19, wherein the clinical sample is saliva.

29. The method of claim 19, wherein the conjugation reagent is glutaric aldehyde.

30. The method of claim 19, wherein the conjugation reagent is formaldehyde.

31. The method of claim 19, wherein the quenching reagent is a mixture of Tris or a salt thereof and ethanolamine.

32. The method of claim 19, wherein the quenching reagent is Tris or a salt thereof.

33. The method of claim 19, wherein the quenching reagent is ethanolamine.

34. The method of claim 1, further comprising the step of neutralizing said biological fluid sample prior to step 1.

35. The method of claim 34, wherein said neutralized biological fluid sample has a pH of about 8.0.

36. The method of claim 1, wherein said hapten further comprises an imine.

37. The method of claim 1, further comprising the step of adding exogenous polypeptides to said biological fluid sample prior to step 1.

38. The method of claim 19, further comprising the step of neutralizing said biological fluid sample prior to step 1.

39. The method of claim 38, wherein said neutralized biological fluid sample has a pH of about 8.0.

40. The method of claim 19, wherein said hapten further comprises an imine.

41. The method of claim 19, further comprising the step of adding exogenous polypeptides to said biological fluid sample prior to step 1.

* * * * *